(12) United States Patent
Assell et al.

(10) Patent No.: US 11,278,336 B2
(45) Date of Patent: Mar. 22, 2022

(54) OSTEOMEDULLARY TISSUE PROCESSING SYSTEM

(71) Applicant: Fortus Medical, Inc., Minneapolis, MN (US)

(72) Inventors: Robert Assell, Minneapolis, MN (US); Andy Freeman, Minneapolis, MN (US)

(73) Assignee: Fortus Medical, Inc., Minneapolis, MN (US)

( * ) Notice: Subject to any disclaimer, the term of this patent is extended or adjusted under 35 U.S.C. 154(b) by 181 days.

(21) Appl. No.: 16/298,438

(22) Filed: Mar. 11, 2019

(65) Prior Publication Data
US 2019/0290344 A1 Sep. 26, 2019

Related U.S. Application Data

(60) Provisional application No. 62/646,519, filed on Mar. 22, 2018.

(51) Int. Cl.
*A61B 17/88* (2006.01)
*A61F 2/46* (2006.01)
*A61L 27/36* (2006.01)

(52) U.S. Cl.
CPC ...... *A61B 17/8822* (2013.01); *A61B 17/8825* (2013.01); *A61B 17/8833* (2013.01);
(Continued)

(58) Field of Classification Search
CPC . A61B 17/88; A61B 17/8802; A61B 17/8805; A61B 17/8822; A61B 17/8825;
(Continued)

(56) References Cited

U.S. PATENT DOCUMENTS 4,969,870 A 11/1990 Kramer
5,152,763 A * 10/1992 Johnson ............. A61B 17/1635
606/86 R
(Continued)

FOREIGN PATENT DOCUMENTS

DE 19949866 A1 11/2001
WO 1999/59500 A2 11/1999

OTHER PUBLICATIONS

McLain, et al. "Transpedicular aspiration of osteoprogenitor cells from the vertebral body: progenitor cell concentration affected by serial aspiration", The Spine Journal, Oct. 19, 2009, vol. 9, No. 12, pp. 995-1002.
(Continued)

*Primary Examiner* — Eric S Gibson
(74) *Attorney, Agent, or Firm* — Michael A. Bondi; Moss & Barnett

(57) ABSTRACT

A bone graft preparation and delivery system including a main body shaft, a bone graft matrix, a first end cap, a second end cap and a plunger. The main body shaft has a first end and a second end. The main body shaft has a main body shaft bore that extends between the first end and the second end. The bone graft matrix is placed in the main bore shaft. The first end cap is attachable to the first end. The second end cap is attachable to the second end. The bone graft preparation and delivery system is operable in a bone graft preparation configuration and a bone graft delivery configuration. When the bone graft preparation and delivery system is in the bone graft preparation configuration, the first end cap and the second end cap are attached to the main body shaft. When the bone graft preparation and delivery system is in the bone graft delivery configuration, the plunger is extendable through the main body shaft bore.

7 Claims, 3 Drawing Sheets

(52) U.S. Cl.
CPC .......... *A61F 2/4601* (2013.01); *A61F 2/4644*
(2013.01); *A61B 2017/8838* (2013.01); *A61L 27/3608* (2013.01); *A61L 2430/02* (2013.01)

(58) Field of Classification Search
CPC ............ A61B 17/8833; A61B 17/8836; A61B 2017/8838; A61F 2/46; A61F 2/4601; A61F 2/4644
See application file for complete search history.

(56) References Cited

U.S. PATENT DOCUMENTS

| | | | |
|---|---|---|---|
| 5,269,785 A | 12/1993 | Bonutti | |
| 5,456,267 A | 10/1995 | Stark | |
| 5,807,353 A | 9/1998 | Schmitz | |
| 5,824,084 A * | 10/1998 | Muschler | A61L 27/32 128/898 |
| 6,022,354 A | 2/2000 | Mercuri | |
| 6,049,026 A | 4/2000 | Muschler | |
| 6,132,448 A | 10/2000 | Perez | |
| 6,406,454 B1 * | 6/2002 | Hajianpour | A61M 1/0039 210/106 |
| 6,673,629 B2 | 1/2004 | Yoshimura | |
| 6,723,131 B2 * | 4/2004 | Muschler | A61F 2/4644 623/23.51 |
| 6,981,948 B2 | 1/2006 | Pellegrino | |
| 8,109,919 B2 | 2/2012 | Kraft | |
| 8,137,408 B2 | 3/2012 | Kadiyala | |
| 8,343,133 B2 | 1/2013 | Allee | |
| 8,439,929 B1 * | 5/2013 | Sharratt | A61F 2/4644 606/92 |
| 8,579,912 B2 | 11/2013 | Isaza | |
| 8,852,119 B2 | 10/2014 | Wawrzyniak | |
| 10,342,552 B2 * | 7/2019 | Assell | A61J 1/1487 |
| 10,610,242 B2 * | 4/2020 | Assell | A61J 1/1481 |
| 2002/0058945 A1 | 5/2002 | Steiner | |
| 2002/0082519 A1 | 6/2002 | Miller | |
| 2002/0161449 A1 * | 10/2002 | Muschler | A61L 27/365 623/23.51 |
| 2003/0031695 A1 | 2/2003 | Kadiyala | |
| 2004/0071668 A1 * | 4/2004 | Bays | A61F 2/00 424/93.7 |
| 2005/0101963 A1 | 5/2005 | Merboth | |
| 2005/0130301 A1 | 6/2005 | McKay | |
| 2006/0246150 A1 | 11/2006 | Thorne | |
| 2006/0264964 A1 * | 11/2006 | Scifert | A61B 17/8816 606/92 |
| 2007/0055282 A1 | 3/2007 | Muschler | |
| 2007/0198043 A1 | 8/2007 | Cox | |
| 2008/0103605 A1 | 5/2008 | Kadiyala | |
| 2008/0145392 A1 | 6/2008 | Knaack | |
| 2008/0195115 A1 | 8/2008 | Oren | |
| 2008/0288006 A1 * | 11/2008 | Brannon | A61B 17/742 606/86 R |
| 2009/0014391 A1 | 1/2009 | Leach | |
| 2009/0081689 A1 | 3/2009 | Yamanishi | |
| 2009/0137927 A1 | 5/2009 | Miller | |
| 2009/0187116 A1 | 7/2009 | Noishiki | |
| 2009/0287190 A1 * | 11/2009 | Shippert | A61M 1/0056 604/542 |
| 2011/0257557 A1 | 10/2011 | Pesce | |
| 2012/0116247 A1 * | 5/2012 | Wawrzyniak | A61B 10/025 600/567 |
| 2013/0030547 A1 | 1/2013 | Burkinshaw | |
| 2013/0131545 A1 | 5/2013 | Azimpoor | |
| 2014/0100574 A1 | 4/2014 | Bono | |
| 2014/0105960 A1 | 4/2014 | Zoldan | |
| 2014/0257133 A1 | 9/2014 | Landrigan | |
| 2014/0274894 A1 | 9/2014 | Leach | |
| 2014/0363403 A1 | 12/2014 | Segina | |
| 2015/0110890 A1 * | 4/2015 | Assell | A61L 27/365 424/549 |
| 2015/0164949 A1 * | 6/2015 | Sowemimo-Coker | A61K 35/19 424/93.7 |
| 2015/0182268 A1 | 7/2015 | Donner | |
| 2016/0324530 A1 * | 11/2016 | Assell | A61J 1/1487 |
| 2016/0325018 A1 * | 11/2016 | Assell | A61M 1/0056 |
| 2016/0331878 A1 | 11/2016 | McGillicuddy | |
| 2018/0064852 A1 * | 3/2018 | Assell | A61L 27/3821 |
| 2018/0353206 A1 | 12/2018 | Assell | |
| 2019/0262050 A1 * | 8/2019 | Assell | A61M 1/0056 |
| 2019/0290344 A1 * | 9/2019 | Assell | A61B 17/8825 |
| 2020/0197024 A1 * | 6/2020 | Assell | C12M 33/14 |

OTHER PUBLICATIONS

Duguy N., et al.: "Biomaterials and osseous regeneration", Annales De Chirurgie Plastique Esthetique, Expansion Scientifique Francaise, Paris, France, vol. 45, No. 3, Jun. 1, 2000, pp. 364-376, Issn: 0294-1260.
Ripamonti U., et al., "Tissue Engineering of Bone by Osteoinductive Biomaterials", MRS Bulletin, Pittsburgh, US, vol. 21, No. 11, Nov. 1, 1996, XP008005014, pp. 36-39.
Kurita, et al., "Differential Effects of Three Preparations of Human Serum on Expansion of Various Types of Human Cells", American Society of Plastic Surgeons, Dec. 20, 2007, 12 pgs.
International Preliminary Report on Patentability received for PCT Serial No. PCT/US2019/021616 dated Oct. 1, 2020, 8 pgs.
Final Office Action received for U.S. Appl. No. 15/996,765 dated Nov. 24, 2020, 18 pgs.
International Search Report and Written Opinion dated Jul. 2, 2019 in PCT/US2019/021616, 12 pgs.
International Search Report and Written Opinion received for PCT Serial No. PCT/US2021/018570 dated May 7, 2021, 9 pgs.

* cited by examiner

OSTEOMEDULLARY TISSUE PROCESSING SYSTEM

REFERENCE TO RELATED APPLICATION

This application claims priority to Provisional Applic. No. 62/646,519, filed on Mar. 22, 2018, the contents of which are incorporated herein by reference.

FIELD OF THE INVENTION

The invention relates generally a tissue processing system. More particularly, the invention relates to an osteomedullary tissue processing system.

BACKGROUND OF THE INVENTION

In the US, bone grafts are most commonly used in spinal fusion surgery and, more generally, in the fusion or arthrodesis of any skeletal joint. In addition, bone graft is generally used in trauma surgery for the treatment of fresh fractures and non-unions, which are typically identified as fractures within 6 months that have not healed properly. The bone graft materials typically bridge a gap between bone segments and may also provide a three-dimensional scaffold on which the bone can grow.

Bone graft treatment is also typically used in conjunction with fresh fractures where the bone has been shattered or where the patient is at a very high risk of developing a non-union fracture. Because many fractures are not this severe and can be treated with alternative methods of fixation, bone grafts are not frequently needed during fresh fracture treatments.

Two areas where bone grafts are used are in conjunction with joint reconstruction and joint revision. For example, the bone graft may be used to fill a void between the bone and joint implant in a joint reconstruction surgery. Joint revision is much more likely to need a bone graft because a large void may result from the removal of the original implant. Joint revisions that use bone graft material therefore usually require a relatively large quantity of the bone graft material.

There are different types of bone graft materials that may be used to assist a patient's body in bone regeneration. These bone graft materials are typically classified as either natural or synthetic materials.

Natural bone graft materials are classified in the following groups. Autograft is bone graft material that is obtained from the same individual that will receive the bone graft material. Allograft is bone graft material that is obtained from another human source, which typically is from cadavers. Xeongraft is bone graft material that is obtained from another species.

Bone grafts can also be categorized by their bone-forming properties as osteoconductive, osteoinductive or osteogenic. Osteoconductivity is the ability of a material to provide an appropriate scaffold or matrix upon which new bone tissue can form. Osteoinductivity is the ability of a material to stimulate the patient's own system to form new bone. Osteogenic material generates new bone tissue itself. Osteoblasts, which can be found in bone marrow and mesenchymal cells, are the only cells that can create new bone.

Autograft bone has historically been the standard of care because of its osteoconductive, osteoinductive and osteogenic properties. At the time of surgery, bone is taken from a donor site in the patient, often the iliac crest bone but others are used, and then is re-implanted back into the patient at the surgical site.

Autograft is often not used, because obtaining the graft generally requires a second surgical procedure with associated risks and expenses. The autograft also typically results in significant post-operative issues, most significantly pain. An additional type of autograft, concentrated cells from bodily fluids such as blood or bone marrow, is often used as well.

In addition to autograft, many other types of bone graft are used including processed cadaver bone, i.e., allograft, in the form of demineralized bone matrix and also so called "living cell" or "stem cell" allograft. Additionally, constituents known to be involved in new bone formation, such as bone morphogenic proteins, typically produced by recombinant processing means, as used. Synthetic materials such as tri-calcium phosphate, calcium sulphate, hydroxyapatite and others are used as well.

Summary of Bone Graft Characteristics by Material

| Type | Osteo-conductive | Osteo-inductive | Osteo-genic |
| --- | --- | --- | --- |
| Autograft | Yes | Yes | Yes |
| Bone morphogenic proteins | No | Yes (strong) | No |
| Demineralized bone matrix | Yes | Minimal | No |
| Allogeneic stem cell | Yes | Unknown | Yes |
| Bone marrow aspirate | No | Yes (strong) | Yes |
| Synthetics | Yes | No | No |

Bone graft substitutes also fall within the classification of bone filler materials. Examples of bone graft substitutes include collagen, polymers such as silicone and some acrylics, hydroxyapatite, calcium sulfate and ceramics.

Bone cement (such as polymethylmethacylate) can be used as a bone void filler to treat bone voids or defects. For example, it can be used to repair fractured bones and vertebral bodies. The bone cement can be used either in procedures that involve direct injection of the bone cement into the fractured vertebral body (i.e., vertebroplasty) or injection of the bone cement into the vertebral body after the height of the vertebral body is restored using a pressurized balloon (i.e., kyphoplasty).

One of the disadvantages of using bone cement is that, once it is injected inside the patient, the bone cement is an inorganic material and, as such, is treated as a foreign body. As such, the bone cement may not only negatively impact healing but can also lead to bone disease.

Additionally, the bone cement is typically stiffer than bone, which may increase the incidence of adjacent level fractures in the spine. Bone cement leakage may cause complications, and has been reported to occur in vertebroplasty and kyphoplasty procedures. If leakage does occur, the bone cement can cause soft tissue injury due to the high temperatures of the exothermic polymerization reaction. In addition, if the bone cement is forced into the vascular system, it can cause emboli.

Bone marrow and bone marrow aspirate concentrate are considered to have a significantly higher bioactivity than circulating blood or concentrated blood known as platelet rich plasma. These features mean that bone marrow is often viewed as being superior to platelet rich plasma for use in orthopedic applications such as spinal fusion and trauma surgery because the bone marrow contains progenitor cells and multipotent stem cells, which assist in the formation of new bone.

Bone marrow aspirate concentrate has become increasingly popular in bone growth applications, particularly spinal fusion and trauma surgery, because of its osteogenic properties. Traditionally, autograft was the gold standard grafting material in these procedures due to the presence of osteoblasts and osteogenic precursor cells, as well as its osteoconductive and osteoinductive properties.

To avoid the risks associated with autograft procurement such as donor site infection and morbidity, bone marrow aspirate concentrate has been increasingly used because it has properties that are similar to autograft and allows surgeons and patients to avoid autograft procurement.

Muschler, U.S. Pat. Nos. 5,824,084 and 6,049,026, both disclose systems for preparing bone graft in which a bone marrow suspension is passed through a porous, biocompatible implantable matrix. Muschler indicates that the bone graft can be prepared intra operatively for use in a person from which the bone marrow aspirate was obtained.

Muschler, U.S. Pat. No. 6,723,131, discloses a system for preparing bone graft. A porous, biocompatible implantable matrix is placed in a hollow column having caps at opposite ends. Bone marrow aspirate is placed in a syringe, which is attached to one of the caps, and then the syringe is used to urge the bone marrow aspirate through the porous, biocompatible implantable matrix.

SUMMARY OF THE INVENTION

An embodiment of the invention is directed to a bone graft preparation and delivery system that includes a main body shaft, a bone graft matrix, a first end cap, a second end cap and a plunger. The main body shaft has a first end and a second end. The main body shaft has a main body shaft bore that extends between the first end and the second end. The bone graft matrix is placed in the main bore shaft. The first end cap is attachable to the first end. The second end cap is attachable to the second end. The bone graft preparation and delivery system is operable in a bone graft preparation configuration and a bone graft delivery configuration. When the bone graft preparation and delivery system is in the bone graft preparation configuration, the first end cap and the second end cap are attached to the main body shaft. When the bone graft preparation and delivery system is in the bone graft delivery configuration, the plunger is extendable through the main body shaft bore.

Another embodiment of the invention is directed to a method of preparing bone graft. A bone graft preparation chamber is provided having a first end, a second end and a bore that extends between the first end and the second end. A bone graft matrix is placed in the bore. A first end cap is attached to the first end. A second end cap is attached to the second end. Osteomedullary tissue is passed through the bone graft preparation chamber to from a bone graft. The first end cap and the second end cap are detached from the bone graft preparation chamber. A plunger is extended through the bore to eject the bone graft from the bone graft preparation chamber.

Another embodiment of the invention is directed to an implant hydration system that includes a biological implant, a first chamber portion and a second chamber portion. The first chamber portion has a first port. The second chamber portion has a second port. The second chamber portion is selectively engagable with the first chamber portion. At least one of the first implant chamber portion and the second chamber portion have a recess formed therein that is adapted to receive the biological implant.

Another embodiment of the invention is directed to a method of hydrating a biological implant. An implant hydration chamber is provided having a first chamber portion and a second chamber portion. The first chamber portion has an inlet port. The second chamber portion has an outlet port. A biological implant is placed between the first chamber portion and the second chamber portion. Osteomedullary tissue is flowed from the inlet port to the outlet port. As the osteomedullary tissue flows from inlet port to the outlet port, the osteomedullary tissue passes through the biological implant.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
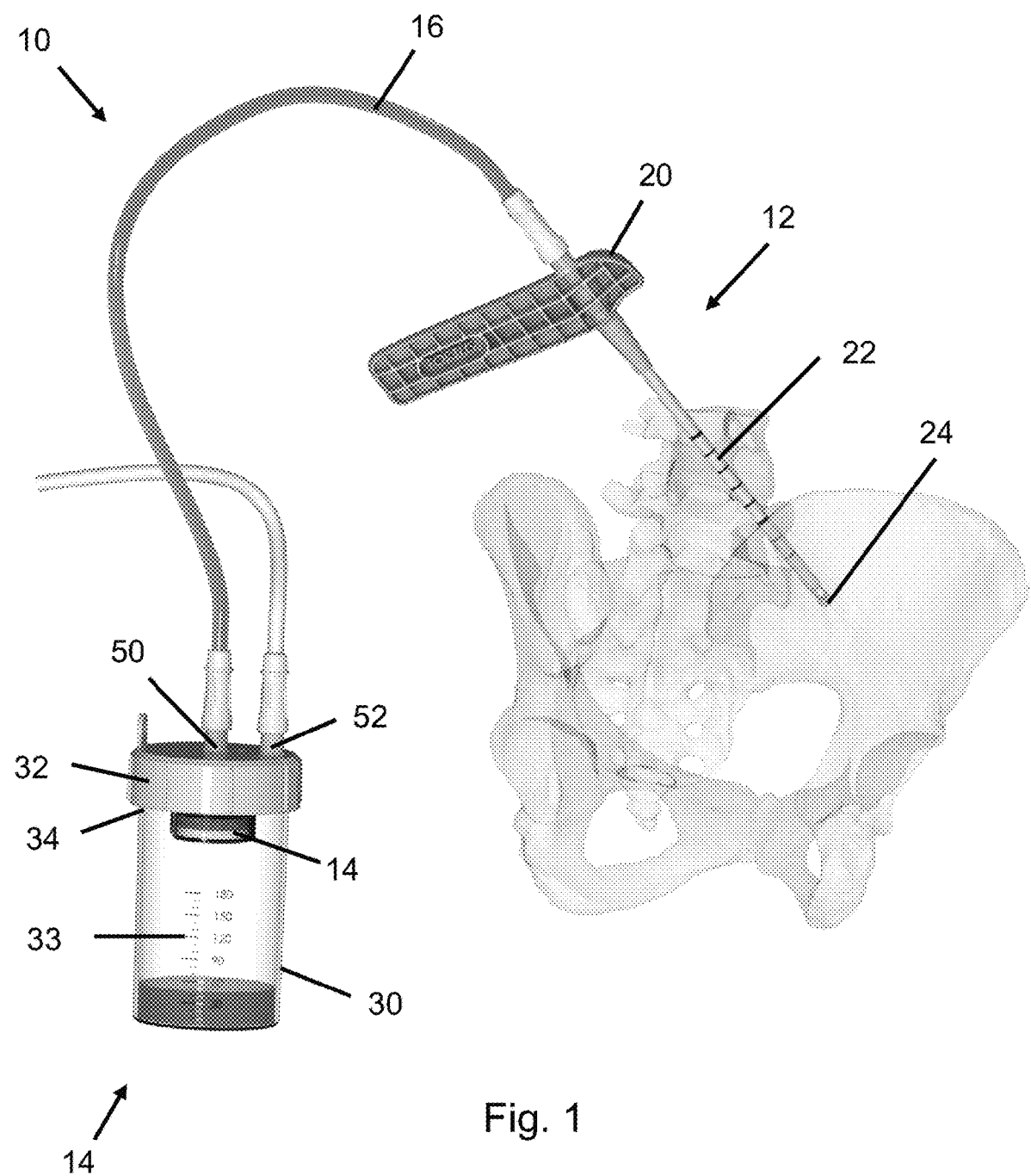
FIG. 1 is a side view of a bone marrow aspiration and processing system according to an embodiment of the invention.

An embodiment of the invention provides a completely autologous process that enables use of the patient's own tissue. The invention enables high yield harvesting of bone fragments, stem and progenitor cells in a process that is safe, fast and efficient. This tissue and bone fragments are used in conjunction with an osteoconductive matrix to form a bone graft.

As an initial step in preparing the bone graft, bone marrow is harvested. In certain embodiments, the bone marrow is harvested from the patient in which the bone graft is intended to be used. Such a process minimizes the potential of incompatibilities when the bone graft is implanted in the patient.

The harvesting device 12 includes a handle portion 20 and a needle portion 22 that are operably connected to each other. In certain embodiments, the needle portion 22 is detachably connected to the handle portion 20. In other embodiments, the needle portion 22 is integrally formed with the handle portion 20.

In certain embodiments, the needle portion 22 may have an outer diameter of about 6 millimeters. Forming the needle portion with this diameter minimizes the potential that bone fragments will become stuck while being drawn through the needle portion 20 during the aspiration process.

The needle portion 22 having the preceding characteristics may have a two-part configuration. An inner portion of the needle portion 22 may include an inner shaft and an outer shaft. The inner shaft may be fabricated from a metallic material such as stainless steel. The metallic material thereby provides the needle portion 22 with a relatively high strength while having a relatively thin wall thickness.

In certain embodiments, the wall thickness of the metallic material may be less than about 10 thousandths of an inch. In certain embodiments, the wall thickness of the inner shaft is between about 3 and 6 thousandths of an inch. In still other embodiments, the wall thickness of the inner shaft is about 4 thousandths of an inch.

Fabricating the inner shaft with a relatively thin wall thickness allows the inner channel to be relatively wide to facilitate a large flow rate of the tissue and bone fragments therethrough while at the same time having a relatively small outer diameter to minimize the size of the hole that is formed in the bone to access the interior of the bone where the bone fragments are formed and the beneficial tissue is located, which reduces the potential of the patient experiencing pain or other issues at the aspiration location.

The outer shaft may be fabricated from a polymeric material that is molded over the inner shaft. The outer shaft thereby enhances strength of the inner shaft while allowing the needle to deflect during the bone marrow and tissue harvesting process. The combined structure of the inner shaft and the outer shaft provides the needle portion 22 with enhanced torsional strength compared to a needle fabricated only from a metallic material or a polymeric material.

To provide the needle portion 22 with a desired level of sharpness, the needle portion 22 has a tip 24 that is fabricated from a metallic material as the metallic material provides an enhanced sharpness as compared to fabricating the tip from a polymeric material. The tip 24 may be attached to the distal end of the inner tube before the outer tube is molded over the inner tube.

Another advantage of using the polymeric outer shaft over the metallic inner shaft is that it is possible for the bore that extends through the inner shaft to be relatively constant over the length of the needle portion 22. If the needle portion 22 had been fabricated only from a polymeric material, it would have been necessary for the inner diameter to taper when moving from the proximal end to the distal end of the needle portion 22 to facilitate molding of the needle portion 22.

Because of the length of the needle portion 22, such tapering would have resulted in a relatively thick wall proximate the proximal end, a relatively thin wall proximate the distal end or combination thereof. Such differences in wall thickness would have limited the flexing of the needle portion 22 near the proximal end while providing too much flexibility proximate the distal end. Both of these situations would have limited the ability to maneuver the needle during the bone fragment and tissue recovery process.

The sharpened tip 24 facilitates accessing the interior of a bone. Thereafter, the harvesting device 12 may be manipulated to form bone fragments. The sharpened tip 24 also facilitates morselizing tissue inside of the bone and thereby enhances the amount of osteomedullary tissue that can be recovered from a patient. The tissue and bone fragments are aspirated from the patient using the harvesting device 12, which causes the aspirated tissue to be collected in the processing device 14.

Because there is a relatively large concentration of bone fragments that are aspirated through the harvesting device 12, the tip 24 has a plurality of relatively large apertures formed therein. Intermediate each of the apertures is at least one sharpened surface. The at least one sharpened surface facilitates cutting while the needle portion 22 is inserted into and removed from the bone. The at least one sharpened surface also facilitates cutting while the needle portion 22 is axially rotated and/or pivoted.

The processing device 14 generally includes a collection vessel 30 to which a collection vessel cap 32 is operably attached. The collection vessel 30 may be formed with a size based upon the volume of tissue and bone fragments that is anticipated to be aspirated from the patient. In certain embodiments, the collection vessel 30 has a volume of about 180 millimeters.

The collection vessel 30 may have a variety of shapes using the concepts of the invention. In certain embodiments, the collection vessel 30 has a generally cylindrical shape. Using such a shape enables the collection vessel cap 32 to be attached using a rotational motion.

A side of the collection vessel 30 may include at least one volume collected marker 33. The upper marker 33 thereby provides guidance to the person using the invention regarding whether a desired volume of tissue has been collected. In certain embodiments, the volume collected markers may include a series of identifiers that correspond to a conventional volume measuring system such as milliliters.

Proximate an upper end of the collection vessel 30, an opening 34 may be provided. In one such embodiment, the opening 34 is generally circular and has a thread on a surface thereof that can be used when attaching the collection vessel cap 32 to the collection vessel 30. In certain embodiments, the thread may be on an outer surface of the opening 34. A person of skill in the art will appreciate that a variety of other techniques may be used to attach the collection vessel cap 32 to the collection vessel 30.

One aspect of the attachment of the collection vessel cap 32 to the collection vessel 30 is that a substantially air-tight seal is formed when the collection vessel cap 32 is attached to the collection vessel 30 so that a vacuum may be used to draw the aspirated tissue and bone fragments into the collection vessel 30.

The collection vessel 30 may be fabricated from a variety of materials using the concepts of the invention. In one embodiment, at least a portion of the collection vessel 30 is fabricated from a transparent material. Such a configuration enables a person using the bone fragment and tissue harvesting and processing system 10 to not only view the volume of aspirated tissue in the collection vessel 30 but also other characteristics of the aspirated tissue such as a color of the aspirated tissue and/or the presence of discrete regions in the aspirated tissue.

Another criterion for the material that is used in fabricating the collection vessel 30 is that the material be biologically compatible and facilitate sterilization of the collection vessel 30 prior to use. An example of one such material that may be used to fabricate the collection vessel 30 is polyethylene terephthalate.

The collection vessel cap 32 may have a generally cylindrical configuration with an inner diameter that is selected based upon an outer diameter of the collection vessel 30 proximate the threaded region to facilitate removable attachment of the collection vessel cap 32 to the collection vessel 30. In this regard, the collection vessel cap 32 may include a thread on an inner surface thereof that is shaped generally complementary to the thread on the collection vessel 30.

While not illustrated, at least a portion of the outer surface of the collection vessel cap 32 may have a shape and/or texture that enhances the ability to grasp the collection vessel cap 32 and turn the collection vessel cap 32 with respect to the collection vessel 30. Because of the nature of the invention and the potential desire to remove the collection vessel cap 32, the collection vessel cap 32 is typically intended to be tightened and loosened using manual force.

The collection vessel cap 32 includes a first port 50 and a second port 52 formed therein. A person of skill in the art will appreciate that at least one of the first port 50 and the second port 52 may alternatively be formed in the collection vessel 30.

The first port 50 includes a connector that facilitates attachment to the tubing 16. In certain embodiments, the first port 50 enables tubing to be attached and detached. When the tubing is attached, a substantially gas-impervious seal is formed. The first port 50 may include a standardized connector profile that enables a variety of objects to be attached thereto. An example of one suitable standardized connector is marketed under the identifier Leur Lock.

Similar to the first port 50, the second port 52 may be formed with a standardized connector profile. An example of one such connector profile that can be used for the second port 52 is a tapered push-on connector that facilitates a friction connection. In such embodiments, the push-on connector includes a plurality of ridges, which reduce the potential of the tubing or other object becoming detached from the second port 52.

The collection vessel cap 32 may be fabricated from a variety of materials using the concepts of the invention. In one embodiment, at least a portion of the collection vessel cap 32 is fabricated from a transparent material.

Another criterion for the material that is used in fabricating the collection vessel cap 32 is that the material be biologically compatible and facilitate sterilization of the collection vessel cap 32 prior to use. An example of one such material that may be used to fabricate the collection vessel cap 32 is polyethylene terephthalate.

A filter container may be provided in the processing device 14. The filter container is positioned so that as the tissue and bone fragments flow through the first port 50, these components pass through the filter container. In certain embodiments, the filter container is attached to an inner surface of the collection vessel cap 32. The filter container may be removably attached to the collection vessel cap 32 such as using a threaded mechanism.

In other embodiments, the filter container may be attached to an outer surface of the collection vessel cap 32. In such an embodiment, the first port 50 may be directly attached to the filter container. In still other embodiments, the filter container may be separate from the processing device 14. In this configuration, the tubing 16 is attached to the filter container. Another section of tubing (not shown) attaches the filter container outlet to the first port 50.

The filter container may have a volume that is significantly smaller than the volume of the processing device 14. In certain embodiments, the filter container has a volume of less than about 20 cubic centimeters. In other embodiments, the volume of the filter container is about 15 cubic centimeters.

A surface of the filter container may have perforations formed therein. In certain embodiments, a lower surface of the filter container may be perforated having a plurality of openings formed therein. The size of the openings may be selected to retain substantially all of the bone fragments in the filter container as the tissue and bone fragments are aspirated from the patient. On the other hand, the openings are sufficiently large so that the liquid in the aspirated is permitted to flow through the lower surface and into the collection vessel 30. The perforations thereby affect physical separation of the aspirate.

In certain embodiments, the lower surface is integrally formed with the other components of the filter container. In other embodiments, the lower surface may be removably attached to the filter container such as using a threaded mechanism. This threaded mechanism may be similar to the threaded mechanism that is used to attach the filter container to the collection vessel cap 32.

A filter material may be placed in the filter container. The filter material is selected with a pore size such that substantially all of the bone fragments are retained in the filter material. The filter material may also be selected to retain at least a portion of the beneficial cells in the tissue. In certain embodiments, the filter material retains substantially all of progenitor cells in the extracted tissue.

The filter material may thereby provide physical separation of the bone fragments from the remainder of the material in the aspirate. Such a separation mechanism is referred to as physical separation. The filter material may also have an affinity for the beneficial components in the aspirate such that as the beneficial components flow past the filter material, the beneficial components are attached to the filter material so that the beneficial components retained in the filter container would be included in the bone graft fabricated therefrom.

As an alternative to providing a relatively homogeneous filter material in the filter container, it is possible for the filter material to include more than one region. For example, there may be a top filter material portion and a bottom filter material portion. The top filter material portion may have a predisposition for retaining the bone fragments therein. The bottom filter material portion may have a predisposition for retaining the beneficial portions of the tissue therein.

In addition to or as an alternate to the filter material described above, the filter container may have a filter membrane that is fabricated with a pore size that retains a desired portion of the bone fragments and the tissue within the filter container. For example, forming the filter membrane with a pore size of between about 20 microns and about 100 microns would facilitate retaining the bone fragments and a substantial portion of the progenitor cells in the filter container.

In yet another configuration, the filter container is selected to retain the bone fragments therein but substantially all of the remainder of the tissue flows into the collection vessel 30. The tissue in the collection vessel 30 may thereby include in addition to progenitor cells, red blood cells and other components that are not needed or potentially detrimental to forming the bone void filler. In such a situation, the red blood cells may be caused to separate from the remainder of the tissue such as mixing a material that causes the red blood cells to agglomerate and settle to the bottom of the collection vessel 30. More details on such a process are described later in this application.

Because of the challenges in aspirating the tissue that is collected in the collection vessel 30, it is desirable for substantially all of the tissue to be retained in the collection vessel 30 for further processing. To reduce the potential of loss of the aspirated tissue that is collected in the bone fragment and tissue harvesting and processing system 10, a hydrophilic membrane valve (not shown) may be attached to the second port 52 intermediate the processing device 14 and the vacuum source.

The hydrophilic membrane valve allows the vacuum to pull gas therethrough until the hydrophilic membrane becomes wet such as when the bone fragment and tissue harvesting and processing system 10 is knocked over or the bone fragment and tissue harvesting and processing system 10 is overfilled with liquid. The hydrophilic membrane valve thereby prevents the aspirated tissue from being drawn out of the bone fragment and tissue harvesting and processing system 10.

To minimize the potential of the processing device 14 being moved from a vertical orientation, the processing device 14 may be placed in a base 56 having a width that is greater than the width of the processing device 14. An example of one suitable technique that may be used to retain the processing device 14 in a vertical orientation is described herein.

An alternative or additional technique to minimize the potential of aspirated tissue being drawn into the vacuum line may include attaching the processing device 14 to an object proximate to the patient from which the tissue is being aspirated. An example of one suitable option is a clip that attaches the processing device 14 to an IV pole, a drape near the patient or the operating table.

The processing cover 42 is sized for slidable movement in the collection vessel 30. The processing cover 42 thereby substantially encloses an upper end of the collection vessel 30 while facilitating changing of the volume enclosed therein.

The processing cover 42 thereby has a shape that generally conforms to the shape of an inner wall of the collection vessel 30 but is formed with a diameter that is slightly smaller than the inner diameter of the collection vessel 30.

The processing cover 42 is fabricated from a material that is less dense than the tissue fluid such that as the fluid is collected in the collection vessel 30 increases, the processing cover 42 raises in the collection vessel 30. In one such embodiment, the processing cover 42 is substantially hollow.

The processing cover 42 has a height that is sufficiently large so that the processing cover 42 is restricted to only moving in a generally vertical direction. In one such embodiment, a height of the processing cover is at least about ⅓ of an inner diameter of the collection vessel 30.

As is described in more detail herein, a vacuum is used to cause the tissue and bone fragments to be aspirated from the patient. Because there is no seal between the processing cover 42 and the collection vessel 30, the vacuum does not affect the position of the processing cover 42 in the collection vessel 30. Rather, the vacuum has a substantially equal force throughout the interior of the collection vessel 30.

The processing cover 42 has a connection port 84 that facilitates attachment of tubing 86 to the processing cover 42. The processing cover 42 also includes a bore (not shown) that extends from the connection port 84 to a lower surface of the processing cover 42. The configuration of the processing cover 42 thereby facilitates material in the collection vessel 30 to be withdrawn through the tubing 86. This process causes the material in the collection vessel 30 that is proximate the processing cover 42 to be withdrawn through the tubing 86. As the material is withdrawn from the collection vessel 30, the processing cover 42 moves with respect to the collection vessel 30.

An end of the tubing 86 opposite the processing cover 42 engages the first port 50 on a lower surface of the collection vessel cap 32 so that fluid that is harvested from the patient flows through tubing 16, then through the tubing 86 and is deposited in the collection vessel 30.

The tubing 86 may have a relatively small inner diameter such as between about 1 and about 5 millimeters. At least a portion of the tubing 86 may be fabricated from a transparent material to evaluate the characteristics of the material being withdrawn through the tubing 86. This combination of the tubing small inner diameter and the transparent nature facilitates separation of the beneficial components in the withdrawn tissue from the red blood cells, which will remain in the collection vessel 30 using the process, which is described in more detail herein.

Prior to use, the components of the processing device 14 may be sterilized. A person of skill in the art will appreciate that a variety of sterilization techniques may be used. An example of one suitable sterilization technique is exposure of the packaged components to gamma radiation.

As an initial step in harvesting the tissue and bone fragments, the collection vessel cap 32 is attached to the collection vessel 30 so that the processing device 14 looks substantially as illustrated in FIG. 1. The osteomedullary tissue harvesting device 12 is attached to the processing device 14 using the tubing 16. A vacuum source is attached to the second port 52.

A site is selected from which the tissue and bone fragments are to be harvested. It is possible to use the invention in conjunction with harvesting tissue and bone fragments from a variety of bones in a patient. Preferred sites for harvesting the tissue and bone fragments include the iliac crest and pedicle/vertebral bodies.

A guide wire (not shown) may be used to identify a location at which the needle portion 22 is to be extended into the bone. An imaging technique such as a fluoroscope may be used to assist in the placement and orientation of the guide wire. The needle portion 22 is extended over the guide wire and into the bone to access the area where the osteomedullary tissue is located.

During the process of aspirating the tissue and bone fragments, the needle portion 22 may be partially withdrawn and then reinserted in a different direction. Such a process increases the amount of bone fragments and osteomedullary tissue that is harvested from the patient. Using such a process it is desirable for the needle to flex but at the same time not break or remain in a deformed/deflected configuration.

During the aspiration process it is important for the relatively liquidy morselized tissue to be aspirated along with the bone fragments. Such a process minimizes the potential of the bone fragments becoming stuck while passing through the harvesting device 12 and the tubing 16 before reaching the collection vessel.

The aspiration process thereby depends on the formation of relatively small bone fragments, which is primarily caused by contact between the needle tip 24 and the harder areas inside the bone. The movement of the needle tip 24 through the interior of the bone also causes morselizing of the tissue inside the bone and such morselizing causes the tissues to become more liquidy.

A vacuum is applied to the system. The person using the system may control application of the vacuum to the needle portion 22 using a variety of techniques. An example of one mechanism to control the vacuum level is using a valve that is operably attached to the vacuum line that is attached to the first port 50.

The aspirated tissue and bone fragments flow through the tubing 14 and into the processing device 14, where the aspirated tissue and bone fragments accumulates in the collection vessel 30. This process is continued until a desired volume of tissue and bone fragments have been aspirated from the patient.

If it is not possible to obtain a desired volume of the tissue and bone fragments from a particular location, it may be necessary to insert the needle portion 22 into a different location in the bone. Alternatively or additionally, it may also be necessary to insert the needle portion 22 into a different bone.

During the process of collecting the aspirated tissue and bone fragments in the processing device 14, it may be desirable to utilize a filter to separate the bone fragments from the other components in the aspirate so that the bone fragments can be utilized in forming the bone graft. A person of skill in the art will appreciate that a variety of techniques may be used to separate the bone fragments from the remainder of the aspirate.

As an initial step in recovering the beneficial components from the aspirated tissue, it may be desirable for the red blood cells to be separated from the other components in the aspirated tissue. One technique that may be used to separate the red blood cells from the other portions of the aspirated tissue is by agglomerating the red blood cells. Once the red blood cells are agglomerated, they become denser than the other materials in the aspirated tissue and thereby settle in the collection vessel. An advantage of using the red blood cell agglomerating technique is that it possible to separate a large portion of the red blood cells while minimizing the potential of damage to the other components in the aspirated tissue.

The red blood cells may be caused to agglomerate using a positively charged material. This positively charged material should be relatively inert with respect to the other desirable components in the aspirated osteomedullary tissue such that the positively charged material does not impact the beneficial properties of the aspirated osteomedullary tissue. Furthermore, the positively charged material should have no negative interactions if any of the positively charged material remains in the aspirated osteomedullary tissue, which then becomes incorporated into the bone graft and thereafter is implanted into the patient.

In certain embodiments, the red blood cell agglomerating material is Prepacyte. The red blood cell agglomerating material is added at a volume so that substantially all of the red blood cells in the aspirated osteomedullary tissue are caused to agglomerate.

The red blood cell agglomerating material is added to the collection vessel 30 such as using a syringe. The volume of the red blood cell agglomerating material that is added to the collection vessel 30 is selected based upon the maximum amount of osteomedullary tissue that is to be collected in the collection vessel 30, as it is believed that an excess amount of the red blood cell agglomerating material does not negatively impact the properties of the osteomedullary tissue.

The time period for substantially all of the red blood cells in the collection vessel 30 to agglomerate may depend on a variety of factors. In certain embodiments, substantially all of the red blood cells agglomerate in less than about 10 minutes after the addition of the red blood cell agglomerating material to the collection vessel 30.

It may be possible to slowly agitate the collection vessel 30 to enhance the dispersal of the red blood cell agglomerating material throughout the aspirated osteomedullary tissue and thereby enhance the rate of the agglomerating process. Once the red blood cells have substantially all agglomerated, the agglomerated red blood cells are allowed to settle in the collection vessel 30.

The syringe is used to withdraw the material other than the agglomerated and settled red blood cells from the collection vessel 30. As this material is withdrawn, the processing cover 42 lowers in the collection vessel 30. The withdrawing is continued until the color of the fluid in the tubing 86 changes from relatively clear to a red color. This change of color is indicative of the agglomerated red blood cells being drawn into the tubing.

It is desired for substantially all of the fluid containing the aspirated tissue to be withdrawn from the collection vessel 30. The relatively narrow inner diameter and the clear material of the tubing 86 enables the person to continue withdrawing the fluid containing the aspirated tissue until a change of color of the fluid in the tubing 86 is identified as that color change indicates that the red blood cells are being drawn into the tubing 86.

Figure 2:
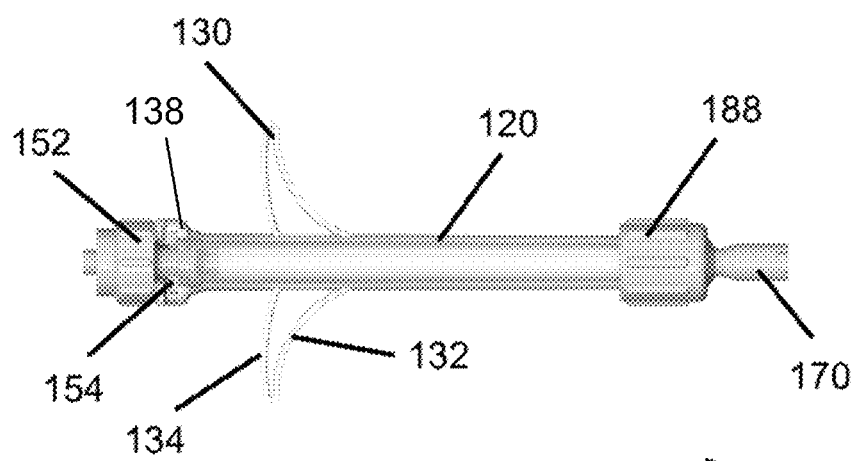
FIG. 2 is a side view of an empty bone graft preparation and delivery chamber according to an embodiment of the invention.
Figure 3:
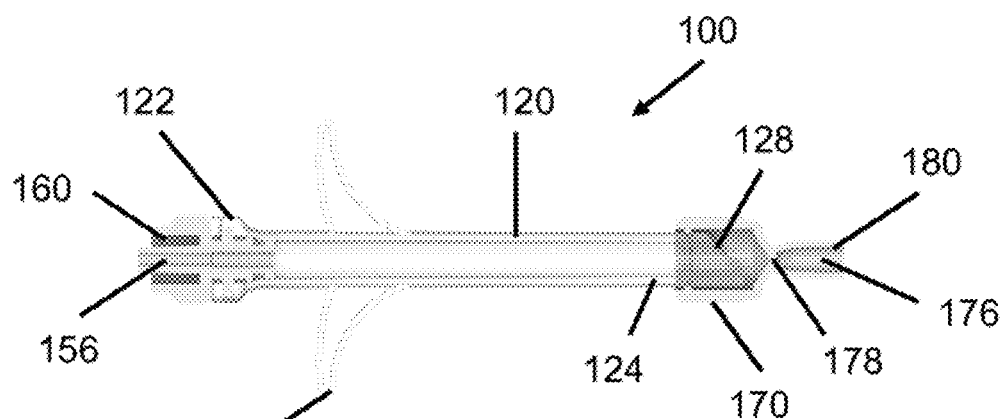
FIG. 3 is a sectional view of the empty bone graft preparation and delivery chamber of FIG. 2.
Figure 4:
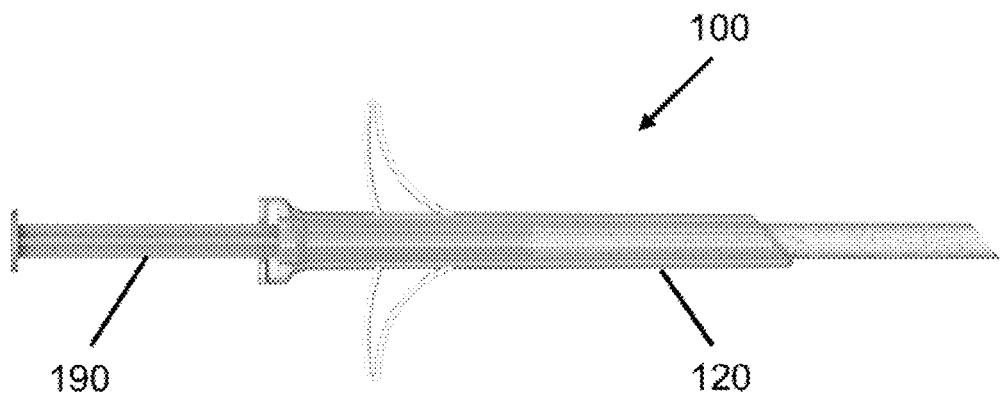
FIG. 4 is a side view of the bone graft being ejected from the bone graft preparation and delivery chamber.
Figure 5:
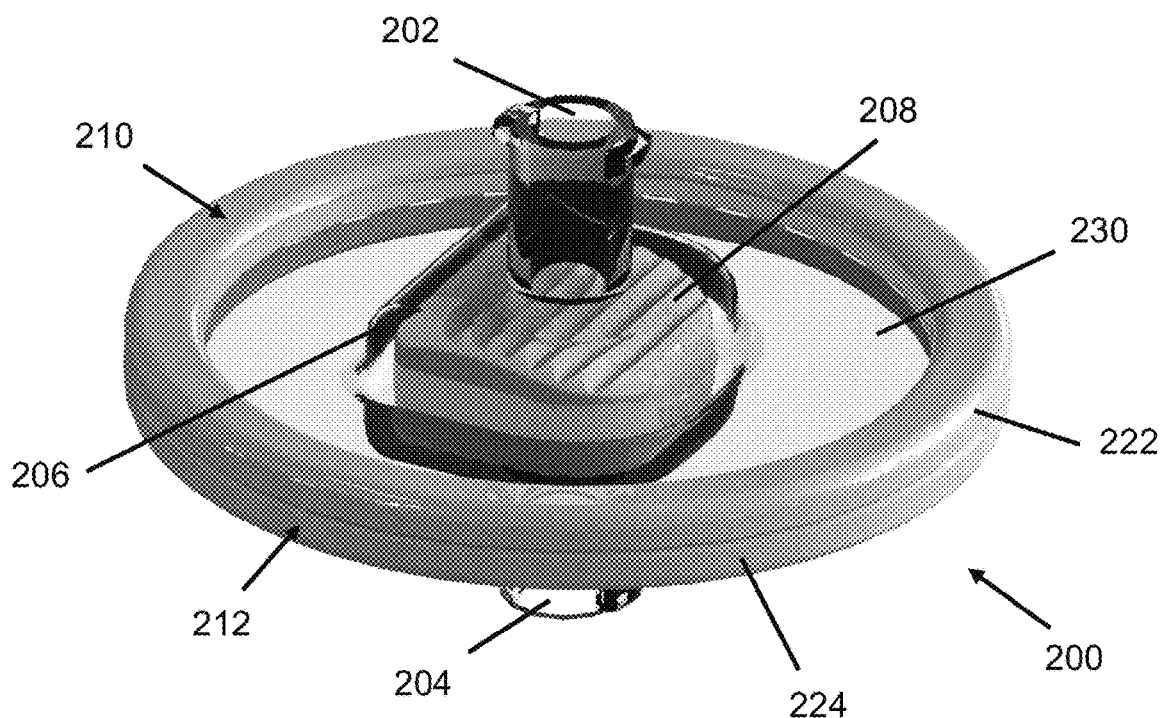
FIG. 5 is a perspective view of an implant hydration chamber.
Figure 6:
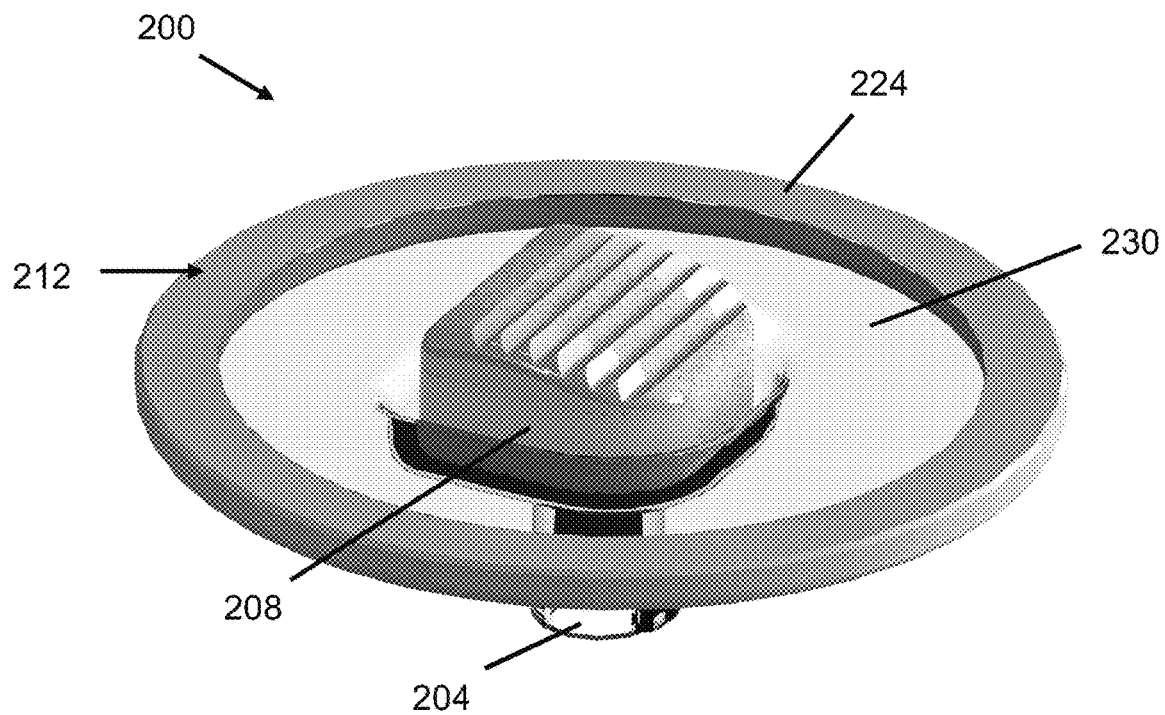
FIG. 6 is a perspective view of the implant hydration chamber of FIG. 5 with a top portion removed therefrom.

The invention is adapted for use in two configurations. In a first configuration, which is illustrated in FIGS. 2-4, the bone graft is in a particulate form that does not have a fixed shape. In a second configuration, which is illustrated in FIGS. 5 and 6, the bone graft is formed into a particular shape.

The syringe is disconnected from the inlet port 50 and a reconfigurable bone graft preparation and delivery chamber 100 is attached between the syringe 74 and the collection vessel 30. The reconfigurable bone graft preparation and delivery chamber 100 generally includes a main body shaft 120 with a first end 122 and a second end 124 at opposite ends thereof, as illustrated in FIGS. 2-4. The main body shaft 120 has a bore 126 that extends between the first end 122 and the second end 124. In certain embodiments, the main body shaft 120 has a generally circular profile.

The bore 126 is fabricated with a volume based upon the volume of the material such as bone graft that is desired to be prepared so that the material substantially fills the bore 126. It is possible to change the volume of the bore 126 using a variety of techniques such as changing an inner diameter of the main body shaft 120 and changing a length of the main body shaft 120.

As the liquid flows through the material placed in the main body shaft 120, the liquid should be substantially evenly distributed. Such distribution is enhanced by having the main body shaft 120 with a length that is substantially longer than the inner diameter of the main body shaft 120.

As used herein, substantially longer means that the length of the main body shaft 120 is greater than about four times bigger than the inner diameter of the main body shaft 120. In other embodiments, the length of the main body shaft 120 is at least about eight times bigger than the inner diameter of the main body shaft 120.

Proximate the second end 124, the main body shaft 120 may have an angled surface 128. In certain embodiments, the angled surface 128 is oriented at an angle of between about 30 degrees and about 60 degrees. Providing the angled surface 128 proximate the second end 124 may enhance the ability to discharge the material from the bone graft preparation and delivery chamber 100, as discussed in more detail herein.

In certain embodiments, at least a portion of the main body shaft 120 is fabricated from a transparent material. In other embodiments, substantially all of the main body shaft 120 is fabricated from the transparent material. Using the transparent material allows the mixing of the materials in the main body shaft 120 to be visually evaluated.

To enhance the ability to discharge material from the main body shaft 120, at least one mechanism is provided on an outer surface of the main body shaft 120 that enhances the ability for a person to grasp the main body shaft 120. In certain embodiments, two arms 130 extend from the main body shaft 120 proximate the first end 122. The arms 130 may be provided on opposite sides of the main body shaft 120.

Each of the arms 130 may be defined by a lower gripping surface 132 and an upper gripping surface 134. The lower gripping surface 132 may have a concave shaft and be angled outwardly when moving towards the first end 122.

The upper gripping surface 134 may have a convex shape and be oriented generally transverse to the main body shaft 120. The lower gripping surface 132 and the upper gripping surface 134 may intersect each other proximate ends thereof that are opposite the main body shaft 120.

The main body shaft 120 may include an increased diameter region 138 proximate the first end. The increased diameter region 138 may enhance the ability to grasp the main body shaft 120 such as when attaching or detaching components to the main body shaft 120.

The increased diameter region 138 may also facilitate enhancing the ability to grasp the reconfigurable bone graft preparation and dispensing chamber 100 when the bone graft is being ejected therefrom as described in more detail herein.

A first connection mechanism 140 is provided for attachment to the first end 122. The first connection mechanism 140 not only seals the first end 122 but facilitates attachment of the reconfigurable bone graft preparation and dispensing chamber 100 to tubing (not shown) that delivers the liquid.

While it is possible for the first connection mechanism 140 to engage the main body shaft 120 using a friction fit technique, a locking technique may be used to minimize the potential of the first connection mechanism 140 inadvertently separating from the main body shaft 120.

In certain embodiments, the locking technique utilizes at least one tab 152 that extends from the first connection mechanism 140. As the first connection mechanism 140 is inserted into the first end 122, the at least one tab 152 passes through an opening (not shown). Rotation of the first connection mechanism 40 with respect to the main body shaft 120 causes the at least one tab 152 to seat in a recess 154 in the first end to prevent the first connection mechanism 140 from separating from the main body shaft 120.

The first connection mechanism 140 has a channel 156 that extends therethrough. An intermediate location on the channel 156 may have a reduced diameter region (not shown). In certain embodiments, the reduced diameter region may have a diameter that is less than about one-quarter of the diameter of other portions of the channel 156. The reduced diameter region reduces the rate on which liquid flows from the first end 122 and thereby causes the liquid to be more evenly distributed through the material that is placed on the main body shaft 120.

Proximate the first end of the channel 156, a connector 160 is provided for attachment of the first connection mechanism 140 to tubing (not shown). A variety of techniques may be used for attaching the tubing to the first connection mechanism 140. An example of one suitable technique is friction fit. Another suitable technique is a connector such as a Leur lock A gasket (not shown) may be provided proximate to where the first connection mechanism 140 engages the main body shaft 120 to substantially prevent liquid introduced into the main body shaft 120 from flowing between the first connection mechanism 140 and the main body shaft 120 and out the first end 122.

At least a portion of an outer surface of the first connection mechanism 140 may have a texture or other structure to enhance the ability of the person to grasp the first connection mechanism 140 and rotate the first connection mechanism 140 with respect to the main body shaft 120 to attach and detach the first connection mechanism 140 and the main body shaft 120.

An example of one suitable texture is a plurality of ridges 168 that extend from the surface of the first connection mechanism 140. The ridges 168 may be provided on the first connection mechanism 140 in a spaced-apart configuration.

A second connection mechanism 170 is provided for attachment to the second end 124. The second connection mechanism 170 not only seals the second end 124 but also facilitates attachment of the reconfigurable bone graft preparation and dispensing chamber 100 to tubing (not shown) that delivers liquid to a collection vessel or a disposal device.

While it is possible for the second connection mechanism 170 to engage the main body shaft 120 using a friction fit technique, a locking technique may be used to minimize the potential of the second connection mechanism 170 inadvertently separating from the main body shaft 120.

In certain embodiments, the first connection mechanism 140 is different than the second connection mechanism 170. Using such a configuration minimizes the potential of the components of the reconfigurable bone graft preparation and delivery chamber 100 being incorrectly attached to each other.

In certain embodiments, the locking technique utilizes mating threads on the inner surface of the second connection mechanism 170 and the outer surface of the main body shaft 120. Rotation of the second connection mechanism 170 with respect to the main body shaft 120 causes the second connection mechanism 170 to be attached to or detached from the main body shaft 120.

The second connection mechanism 170 has a channel 176 that extends therethrough. An intermediate location on the channel 176 may have a reduced diameter region 178. In certain embodiments, the reduced diameter region 178 may have a diameter that is less than about one-quarter of the diameter of other portions of the channel 176. The reduced diameter region 178 reduces the rate on which liquid flows from the second end 124 and thereby causes the liquid to be more evenly distributed through the material that is placed on the main body shaft 120.

Proximate an end of the channel 176, a connector 180 is provided for attachment of the second connection mechanism 170 to tubing (not shown). A variety of techniques may be used for attaching the tubing to the second connection mechanism 170. An example of one suitable technique is friction fit. Another suitable technique is a connector such as a Leur lock.

A gasket (not shown) may be provided proximate to where the second connection mechanism 170 engages the main body shaft 120 to substantially prevent liquid introduced into the main body shaft 120 from flowing between the second connection mechanism 170 and the main body shaft 120 and out the second end 124.

At least a portion of an outer surface of the second connection mechanism 170 may have a texture or other structure to enhance the ability of the person to grasp the second connection mechanism 170 and rotate the second connection mechanism 170 with respect to the main body shaft 120 to attach and detach the second connection mechanism 170 and the main body shaft 20.

An example of one suitable texture is a plurality of ridges 188 that extend from the surface of the second connection mechanism 170. The ridges 188 may be provided on the second connection mechanism 170 in a spaced-apart configuration.

A person of skill in the art will appreciate that a variety of bone graft matrices may be used. The bone graft matrix should be a cell binding and cell friendly, osteoconductive material. The osteoconductive matrix can be allogeneic, synthetic or a combination thereof. The allogeneic material can be provided in a variety of forms. Examples of two such suitable forms are granules and fibers. If bone fragments were collected as discussed above, the bone fragments may be utilized in preparing the osteoconductive matrix.

The osteoconductive matrix that is placed in the reconfigurable bone graft preparation and delivery chamber 100 may include a combination of demineralized bone matrix, a suitable synthetic alternative such as hydroxyapatite with the addition of other materials that fall within the classification of extracellular matrix. Examples of these materials include hyaluronic acid, collagen, keratin, elastin, fibronectin and laminin.

The osteoconductive matrix may include at least one of demineralized bone matrix, a suitable synthetic alternative such as hydroxyapatite with the addition of other materials that fall within the classification of extracellular matrix. Examples of these materials include hyaluronic acid, collagen, keratin, elastin, fibronectin and laminin.

The allograft can be provided as mineralized or demineralized depending on the intended use of the graft. In certain embodiments, the allograft granules have a particle size that is between about 3 millimeters and about 100 microns.

Examples of the synthetic materials include calcium phosphate, tri-calcium phosphate, hydroxyapatite or combinations thereof. The synthetic materials may be provided in a variety of particle sizes such as between about 3,000 microns and 60 microns.

The osteoconductive matrix can be configured as a filter for selective retention of the desirable constituents of red blood cell depleted osteomedullary tissue whereby the osteoconductive matrix filters the desirable constituents by means of mechanical filtering such as by controlled porosity and/or by means of selective surface binding such as affinity chromatography like effect.

In certain embodiments, the combination includes greater than about 50% by weight demineralized bone matrix or synthetic substitute thereof. In other embodiments, the combination includes demineralized bone matrix or synthetic substitute thereof at a concentration of between about 60% and 90% by weight.

The osteoconductive matrix that is used in preparing the bone graft may be provided in a variety of forms such as powder, small particles or in the shape of the implant. The osteoconductive matrix can be obtained from various commercial sources such as AlloSource, Cryolife or RTI Biologics.

In certain embodiments, the osteoconductive matrix may have an average particle size of less than about 1 millimeter. In other embodiments, the osteoconductive matrix may have an average particle size of less than about 0.5 millimeters.

Because of the intended in-vivo use of the bone graft, the osteoconductive matrix should be provided in a sterile configuration to minimize the potential of introducing pathogens during the process of implanting the bone graft. Prior to using the bone graft, the components used to fabricate the bone graft should be relatively uniformly mixed.

The osteoconductive matrix may be compacted when being placed in the cartridge to enhance the uniformity at which the aspirated osteomedullary tissue will pass through the osteoconductive matrix.

In addition to using a chromatography effect to selectively retain the efficacious components in the red blood cell depleted aspirated tissue in the filtering osteoconductive matrix, e.g., a demineralized bone plus extracellular matrix composite, it is also possible to use a mechanical entrapment or filtering effect to selectively retain the efficacious components in the aspirate osteomedullary tissue in the osteoconductive matrix.

The osteoconductive matrix may have a multi-strata configuration. In certain embodiments, the osteoconductive matrix is configured to go from high inherent porosity proximate the inlet to lower inherent porosity proximate the outlet. Alternatively, it may be possible to use a reverse descending strata configuration to help keep the smallest particles in place.

For example, a more coarsely ground osteoconductive matrix may be placed proximate the entry port of the cartridge and more finely ground osteoconductive matrix may be placed proximate the outlet port of the cartridge. It is also possible to put one or more additional layers between the more coarsely ground layer and the more finely ground layer that progressively include more finely ground particles.

The osteoconductive matrix may consist of a thin layer of 250+ micron particles that is placed on the membrane. Next, a slightly thicker layer of 100+ micron particles is placed in the cartridge. This process is repeated with 250+ micron particles, 500+ micron particles, 1,000+ micron particles and 3,000+ micron particles.

The effective porosity of a bed of granules is between about 25 percent and about 30 percent of the granule size. For example, a bed of 100 micron granules will exhibit an effective porosity of about 25 microns to about 30 microns. The typical granule size range of sieved particles can be less than 40 microns, between 60 microns and 100 microns, between 100 microns and 250 microns, between 250 microns and 500 microns, between 500 microns and 1,000 microns, between 1,000 microns and 3,000 microns and greater than 3,000 microns.

The aspirated osteomedullary tissue will be introduced at the first end of the reconfigurable bone graft preparation and delivery chamber 100 and then pass through the 3,000 micron layer and then the 1,000 micron layer and so on. The larger constituents that may be in the aspirated osteomedullary tissue such as small pieces of bone, cartilage or thrombus will be trapped in the first layer but the smaller constituents will pass through all the way down to the stem cell size, which will be trapped in the 60 micron layer or the 100 micron layers as the size of these cells is in the range of 15 to 50 microns.

One beneficial technique for associating the osteomedullary tissue with the osteoconductive matrix is using a syringe. A benefit of using the syringe to cause the suction to be drawn on the second end of the bone graft mixing container is that a sufficient vacuum is applied to cause the osteomedullary tissue to be drawn through the matrix in the osteoconductive matrix without the force being too large such that the osteomedullary tissue is caused to form a channel through the osteoconductive matrix. The force is continued into a desired volume of the osteomedullary tissue is drawn through the osteoconductive matrix. A benefit of this process is that the osteomedullary tissue cells are substantially unaffected and undamaged during the process of forming the osteoconductive matrix.

It is also possible to utilize an affinity mechanism to trap desirable cells in the bone matrix. This process may be a preferred retention mechanism as in certain configurations, it is more discriminating for the preferred cells rather than just size. A person of skill in the art will appreciate that a variety of compositions may be utilized based upon the cells that are desired to be trapped in the bone matrix. For example, the attractant composition may exhibit a charge that causes the desired cells to be attracted to the bone matrix.

Red blood cells have a particle size of about 7 micrometers. White blood cells have a particle size of between about 15 and 18 micrometers. The beneficial osteomedullary and progenitor cells in the bone marrow aspirate have a particle size of between about 35 and 50 micrometers.

As a result of this situation is that the osteomedullary cells have a size that is considerably larger than the other components in the bone marrow aspirate, this size difference can be used to facilitate retention of the osteomedullary cells in the filter container while the much smaller red blood cells and white blood cells pass through the filter container.

In an embodiment, a source containing the aspirated tissue is attached to the first end of the reconfigurable bone graft preparation and delivery chamber 100 and a vacuum or other negative force is applied to the second end to cause the aspirated tissue to be pulled through the bone graft matrix.

In another embodiment, a syringe is depressed to cause the fluid containing the aspirated tissue to pass through the reconfigurable bone graft preparation and delivery chamber 100 from the first end to the second end. The osteoconductive matrix in the reconfigurable bone graft preparation and delivery chamber 100 causes substantially all of the aspirated tissue to be retained thereon to separate the aspirated tissue from the remainder of the fluid.

The system described herein thereby results in the aspiration of a significant amount of bone matrix. This system also results in multiple mechanisms for recovering beneficial cells from within the bone. The first mechanism encompasses the beneficial cells that are associated with the bone fragments. The second mechanism relates to the selective retention of the beneficial cells as the aspirate is passed through the filter container. The third mechanism is from the material that collects in the collection vessel and from which the red blood cells are separated as described in more detail herein.

The combined result of using these three mechanisms enables substantially all of the beneficial cells in the aspirated tissue is recovered. Such recovery represents a significant enhancement when compared to the prior techniques, which in addition to utilizing an inefficient harvesting process, recovered a much smaller percentage of the beneficial cells from the harvested tissue.

Depending on the desired application of the bone paste, the bone paste can be formed with different flowabilities. The flowability of the bone paste can be adjusted by changing the amount of water in the bone marrow aspirate concentrate as well as the amount of water that is allowed to pass through the filter membrane at the second end of the cartridge.

Alternatively to applying the bone graft as a paste, it is possible to form the bone graft material into the desired shape of the implant. After the bone graft material is formed into the desired shape, the moisture content of the bone graft material can be reduced to cause the implant to become more rigid. An example of one technique that may be used to reduce the moisture content of the implant is heating.

The physical properties of the bone graft material may be enhanced by the addition of at least one additive to the bone graft material. An example of one additive is collagen.

The total time from harvesting of the cells from the patient to having a bone graft that is ready for use in the patient can be done in a relatively short period of time. In certain embodiments, the process takes less than one hour. In other embodiments, the process takes between about 30 minutes and about 40 minutes.

Another advantage of the osteomedullary tissue process system described herein is that it is a closed system. Such a closed system facilitates use of the osteomedullary tissue processing system in non-sterile environments such as a doctor's office, as compared to a sterile environment that is typically only found in an operating room.

The beneficial portions of the osteomedullary tissue (progenitor cells) can be retained in a relatively small volume of a bone graft material such as tricalcium phosphate. In certain embodiments, the bone graft material is selected with an effective porosity of between about 20 and 30 percent.

Using such a process, it is possible to prepare a bone graft base that contains the osteomedullary tissue where the level of bone graft material is relatively small compared to the volume of osteomedullary tissue. Proximate to when it is desired to use the bone graft material, the bone graft base is mixed with a primary bone graft material.

In this configuration, the concentration of the primary bone graft material may be greater than the concentration of the base bone graft material. Using such a configuration, a surgeon is able to obtain the benefits associated with using a bone graft that contains osteomedullary tissue while at the same time being able to use a primary bone graft material that the surgeon prefers.

The bone graft base may be fabricated with a relatively low viscosity such that when the bone graft base is mixed with the primary bone graft material, the bone graft thereby produced has a desired viscosity.

The concentration of the bone graft base in the bone graft may be between about 10 percent and about 90 percent. In other embodiments, the concentration of the bone graft base in the bone graft is between about 20 percent and about 50 percent.

The invention results in a purified cell solution that can be used in a number of applications such as bone graft enrichment and stem cell enriched injectable. The concentrated bone marrow cells can also be used in conjunction with a variety of other applications. Examples of these applications include repair of strained or torn ligaments or tendons and restoring early osteoarthritis cartilage loss as well as treating radiculopathy. Such treatments can slow the progression of certain diseases and thereby delay or eliminate the need for surgery. Through the use of the invention patients are able to significantly improve their overall quality of life.

Once the aspirate with the osteomedullary tissue is passed through the reconfigurable bone graft preparation and delivery chamber 100, the bone graft is ready for use. The first connection mechanism 140 and the second connection mechanism 170 are detached from the main body shaft 120 and a plunger 190 is attached to the first end 122 of the main body shaft 120, as illustrated in FIG. 4.

The plunger 190 has a profile and shape that are similar to the inner profile and shape of the main body shaft 120 so that as the plunger 190 is urged through the main body shaft 120, the bone graft is ejected from the second end 124 of the main body shaft 120.

Another aspect of the invention is directed to using the invention to provide stem cell injections such as to treat soft tissue injuries such as tendons, ligaments and cartilage. When the invention is used in conjunction with stem cell injections, the cells can be concentrated from the purified solution. Thereafter, the cells can be re-suspended in an injectable carrier. Similar to the use of the invention in conjunction with bone grafts, this embodiment can be completed in a relatively short period of time such as less than one hour. In other embodiments, the time to prepare the injectable stem cells is between about 30 minutes and about 40 minutes.

At least a portion of the components of the osteomedullary tissue harvesting system may be disposable such that after a single use of the items, the items are discarded. In other embodiments, at least a portion of the components of the osteomedullary tissue harvesting system may be configured to be cleanable and sterilizable such that the components can be reused in subsequent surgical procedures.

It has been found that the preceding process of passing the osteomedullary tissue through the matrix causes about 18 percent of the total nucleated cells to be retained in the matrix and about 89 percent of the progenitor cells to be retained in the matrix. These results indicate that the process described herein represents a significant improvement over the prior art processes for capturing progenitor cells in the osteoconductive matrix and such improvement increases the quality of the bone graft thereby produced.

Another embodiment of the invention is directed to an implant hydration chamber that is illustrated at 200 in FIGS. 5 and 6. The implant hydration chamber 200 comprises an inlet port 202 and an outlet port 204. In certain embodiments, the inlet port 202 is on a location of the implant hydration chamber 200 that is generally opposite a location of the outlet port 204.

The implant hydration chamber 200 has a recess 206 formed therein that is adapted to receive at least one implant 208. The recess 206 may have a shape that at least partially conforms to a shape of the at least one implant 208.

In particular, the shape of the recess 206 substantially prevents material flowing from the inlet port 202 to the outlet port 204 from flowing around the at least one implant 208. Because of this configuration, the material must flow through the at least one implant 208 when moving from the inlet port 202 to the outlet port 204.

The inlet port 202 and the outlet port 204 facilitate attaching the implant hydration chamber 200 to other components that are used in conjunction with the implant hydration process. The connection mechanism should resist inadvertent separation of the components. An example of one suitable connection method that can be used with the inlet port 202 and the outlet port 204 is a Leur lock.

The implant hydration chamber 200 may include a first chamber portion 210 and a second chamber portion 212 that are removably attachable to each other. Using this configuration facilitates placing the implant 208 into the recess 206 and removing the implant 206 from the recess 206.

In certain embodiments, the implant hydration chamber 200 includes a frame member 220 that extends at least partially around a periphery of the implant hydration chamber 200. In other embodiments, the frame member 220 extends substantially around the implant hydration chamber 200. In still other embodiments, the frame member 220 has a generally circular shape. The frame member 220 may facilitate attaching the first chamber portion 210 and the second chamber portion 212 to each other.

The frame member 220 may include a first frame section 222 and a second frame section 224. The first frame section 222 is associated with the first chamber portion 210 and the second frame section 224 is associated with the second chamber portion 212.

The first frame section 222 engages the second frame section 224 to prevent the first chamber portion 210 from separating from the second chamber portion 212. In certain embodiments, the first frame section 222 releasably engages the second frame section 224. Using such a configuration enables the first chamber portion 210 to be separated from the second chamber portion 212 after the implant 208 is hydrated.

A person of skill in the art will appreciate that a variety of techniques may be used for the first frame section 222 to releasably engage the second frame section 224. In another embodiment, the first frame section 222 permanently engages the second frame section 224. Using such a configuration requires at least a portion of the implant hydration chamber 200 to be broken to remove the implant 208 from the implant hydration chamber 200. Such a process prevents reusing the implant hydration chamber 200.

At least a portion of an interior region 230 of the first chamber portion 210 and the second chamber portion 212 may be fabricated from a flexible material. In certain embodiments, the interior regions 230 on the first chamber portion 210 and the second chamber portion 212 adhere to each other when the first chamber portion 210 is placed in engagement with the second chamber portion 212. This configuration minimizes the potential of the material that flows through the implant hydration chamber 200 to flow around the implant 208.

In certain embodiments, at least part of the interior region 230 is fabricated from an elastomeric material. The material selected should have sufficient flexibility to bend to generally conform to an outer surface of the implant 208. In particular, the material should bend to generally conform to the edge of the implant 208 proximate to the intersection of the first chamber portion 210 and the second chamber portion 212.

This configuration substantially prevents fluid that flows from the inlet port 202 to the outlet port 204 from flowing around the implant 208. Rather, the fluid must flow through the implant 208 when flowing from the inlet port 202 to the outlet port 204.

In addition to exhibiting the preceding characteristics, the material that is used to fabricate the interior region 230 should not exhibit negative reactions when in contact with bodily fluids and bodily tissue and should be approved for use with medical devices. Examples of materials that may be used to fabricate the interior region 230 include ethylene vinyl acetate, thermoplastic polyurethane, polyvinyl chloride, Non-DEHP polyvinyl chloride, thermoplastic elastomer, trioctyl trimellitate, Kraton rubber and styrene block copolymers.

In another embodiment, the interior region 230 is fabricated from a thermoset material that bends when being placed around the implant 208 but which becomes rigid after being heated or otherwise cured.

In yet another embodiment, the interior region 230 is molded with a recess formed therein based upon the shape and size of the implant 208 that is intended to be used in conjunction with the implant hydration chamber 200. In this situation, there would need to be several uniquely shaped interior regions 230 that are shaped similar to the implants 208.

The interior region 230 may be permanently attached to the frame member 220. In other embodiments, the interior region 230 may be detachably connected to the frame member 220.

Similar to the embodiment described with respect to FIGS. 2-4, a reduced diameter channel may be provided in the inlet port 202 if the fluid is pulled through the implant hydration chamber 200 by applying a vacuum to the outlet port 204. Alternatively, the reduced diameter channel may be provided in the outlet port 204 if the fluid is pushed through the implant hydration chamber 200 by injecting the fluid to the inlet port 202.

The use of the implant hydration chamber 200 may be similar to the use of the reconfigurable bone graft preparation and delivery chamber 100. The aspirated osteomedullary tissue will be introduced at the first end of the implant hydration chamber 200.

In an embodiment, a source containing the aspirated tissue is attached to the inlet port 202 of the implant hydration chamber 200 and a vacuum or other negative force is applied to the outlet port 204 to cause the aspirated tissue to be pulled through the bone graft matrix.

In another embodiment, a syringe is depressed to cause the fluid containing the aspirated tissue to pass through the implant hydration chamber 200 from the inlet port 202 to the outlet port 204. The implant 208 in the implant hydration chamber 200 causes substantially all of the aspirated tissue to be retained thereon to separate the aspirated tissue from the remainder of the fluid.

A benefit of using the syringe to cause the suction to be drawn on the second end of the implant hydration chamber 200 is that a sufficient vacuum is applied to cause the osteomedullary tissue to be drawn through the implant 208 without the force being too large such that the osteomedullary tissue is caused to form a channel through the implant. The force is continued into a desired volume of the osteomedullary tissue is drawn through the implant 208. A benefit of this process is that the osteomedullary tissue cells are substantially unaffected and undamaged during the process of hydrating the implant.

It is also possible to utilize an affinity mechanism to trap desirable cells in the implant. This process may be a preferred retention mechanism as in certain configurations, it is more discriminating for the preferred cells rather than just size. A person of skill in the art will appreciate that a variety of compositions may be utilized based upon the cells that are desired to be trapped in the implant. For example, the attractant composition may exhibit a charge that causes the desired cells to be attracted to the bone matrix.

The syringe 74 is depressed to cause the fluid containing the aspirated tissue to pass through the implant hydration chamber 200. The implant 208 in the implant hydration chamber 200 causes substantially all of the aspirated tissue to be retained thereon to separate the aspirated tissue from the remainder of the fluid.

The system described herein thereby results in the aspiration of a significant amount of the implant. This system also results in multiple mechanisms for recovering beneficial cells from within the bone. The first mechanism encompasses the beneficial cells that are associated with the bone fragments. The second mechanism relates to the selective retention of the beneficial cells as the aspirate is passed through the implant hydration chamber 200.

The combined result of using these mechanisms enables substantially all of the beneficial cells in the aspirated tissue is recovered. Such recovery represents a significant enhancement when compared to the prior techniques, which in addition to utilizing an inefficient harvesting process, recovered a much smaller percentage of the beneficial cells from the harvested tissue.

Prior to passing the osteomedullary tissue through the chamber containing the bone graft matrix, the osteomedullary tissue may be heated to a temperature of at least about 80° F. In other embodiments, the osteomedullary tissue is heated to a temperature of at least about 90° F. In still other embodiments, the osteomedullary tissue is heated to a temperature of between about 90° F. and about 110° F. In still other embodiments, the osteomedullary tissue is heated to a temperature of about 98° F., which is similar to the in vivo temperature of a human body. It has been found that heating the osteomedullary tissue increases the concentration of the beneficial cells that are retained in the bone graft preparation chamber. This process may be particularly beneficial when there is an extended period of time between aspiration of the osteomedullary tissue and the preparation of the bone graft or where collagen is used in the osteomedullary tissue.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A bone graft preparation and delivery system comprising:
    a main body shaft having a first end and a second end, wherein the main body shaft has a main body shaft bore that extends between the first end and the second end, wherein the second end is oriented at an angle of between about 30 degrees and about 60 degrees;
    a bone graft matrix placed in the main bore shaft;
    a first end cap that is attachable to the first end;
    a second end cap that is attachable to the second end; and
    a plunger, wherein the bone graft preparation and delivery system is operable in a bone graft preparation configuration and a bone graft delivery configuration, wherein when the bone graft preparation and delivery system is in the bone graft preparation configuration, the first end cap and the second end cap are attached to the main body shaft and wherein when the bone graft preparation and delivery system is in the bone graft delivery configuration, the plunger is extendable through the main body shaft bore.

2. The bone graft preparation and delivery system of claim 1, wherein a first attachment mechanism by which the first end cap attaches to the main body shaft is different than a second attachment mechanism by which the second end cap attaches to the main body shaft.

3. The bone graft preparation and delivery system of claim 1, wherein at least one of the first end cap and the second end cap has a bore extending therethrough and wherein the bore has a restricted diameter section.

4. The bone graft preparation and delivery system of claim 1, wherein the bone graft preparation and delivery system further comprises at least one arm extending from the main body shaft.

5. The bone graft preparation and delivery system of claim 4, wherein the at least one arm comprises a lower gripping surface and an upper gripping surface that intersect each other.

6. The bone graft preparation and delivery system of claim 1, and further comprising an osteomedullary tissue delivery source attached to the first end cap.

7. The bone graft preparation and delivery system of claim 6, wherein the osteomedullary tissue delivery source comprises progenitor cell rich plasma that is substantially depleted of red blood cells.

* * * * *